(12) United States Patent
Takahashi et al.

(10) Patent No.: US 12,383,473 B2
(45) Date of Patent: Aug. 12, 2025

(54) OIL-BASED COSMETIC PRODUCT HAVING DECORATIVE LAYER

(71) Applicant: Shiseido Company, Ltd., Tokyo (JP)

(72) Inventors: Kiyoshi Takahashi, Tokyo (JP); Hiromi Oikawa, Tokyo (JP); Ken Hirosaki, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 1081 days.

(21) Appl. No.: 17/418,614

(22) PCT Filed: Dec. 26, 2019

(86) PCT No.: PCT/JP2019/051206
§ 371 (c)(1),
(2) Date: Jan. 21, 2022

(87) PCT Pub. No.: WO2020/138322
PCT Pub. Date: Jul. 2, 2020

(65) Prior Publication Data
US 2022/0142876 A1 May 12, 2022

(30) Foreign Application Priority Data
Dec. 27, 2018 (JP) ................................. 2018-244017

(51) Int. Cl.
| | | |
|---|---|---|
| *A61K 8/02* | (2006.01) | |
| *A61K 8/19* | (2006.01) | |
| *A61K 8/25* | (2006.01) | |
| *A61K 8/29* | (2006.01) | |
| *A61K 8/31* | (2006.01) | |
| *A61K 8/34* | (2006.01) | |
| *A61K 8/37* | (2006.01) | |
| *A61K 8/40* | (2006.01) | |
| *A61K 8/58* | (2006.01) | |
| *A61K 8/67* | (2006.01) | |
| *A61K 8/73* | (2006.01) | |
| *A61K 8/81* | (2006.01) | |
| *A61K 8/891* | (2006.01) | |
| *A61Q 1/02* | (2006.01) | |
| *A61Q 1/12* | (2006.01) | |

(52) U.S. Cl.
CPC ............... *A61K 8/022* (2013.01); *A61K 8/19* (2013.01); *A61K 8/25* (2013.01); *A61K 8/29* (2013.01); *A61K 8/31* (2013.01); *A61K 8/347* (2013.01); *A61K 8/375* (2013.01); *A61K 8/40* (2013.01); *A61K 8/585* (2013.01); *A61K 8/678* (2013.01); *A61K 8/73* (2013.01); *A61K 8/8188* (2013.01); *A61K 8/891* (2013.01); *A61Q 1/02* (2013.01); *A61Q 1/12* (2013.01); *A61K 2800/437* (2013.01); *A61K 2800/48* (2013.01)

(58) Field of Classification Search
CPC . A61K 8/022; A61K 8/19; A61K 8/25; A61K 8/29; A61K 8/31; A61K 8/347; A61K 8/375; A61K 8/40; A61K 8/585; A61K 8/678; A61K 8/73; A61K 8/8188; A61K 8/891; A61K 2800/437; A61K 2800/48; A61K 8/732; A61K 8/0237; A61K 8/37; A61K 8/8111; A61Q 1/02; A61Q 1/12
See application file for complete search history.

(56) References Cited

U.S. PATENT DOCUMENTS

| | | | |
|---|---|---|---|
| 9,078,817 B2 | 7/2015 | Chiba et al. | |
| 2008/0233064 A1* | 9/2008 | Tabakman | A61K 8/375 |
| | | | 424/78.03 |
| 2013/0202665 A1 | 8/2013 | Chiba et al. | |
| 2019/0241759 A1* | 8/2019 | Higashikawa | E04F 13/08 |

FOREIGN PATENT DOCUMENTS

| | | |
|---|---|---|
| JP | 2002-068925 A | 3/2002 |
| JP | 3657148 B2 | 3/2005 |
| JP | 2005-089337 A | 4/2005 |
| JP | 2005-239600 A | 9/2005 |
| JP | 2010-099226 A | 5/2010 |
| JP | 2010-105952 A | 5/2010 |
| JP | 2011-032181 A | 2/2011 |
| JP | 2014-162791 A | 9/2014 |

OTHER PUBLICATIONS

Tanaka (JPH01301611A Machine Translation) (Year: 1989).*

* cited by examiner

*Primary Examiner* — Robert A Wax
*Assistant Examiner* — Quanglong N Truong
(74) *Attorney, Agent, or Firm* — Foley & Lardner LLP

(57) ABSTRACT

The purpose of the present invention is to provide a novel transparent oil-based cosmetic product which, when decorating the transparent oil-based cosmetic product, enables decoration with a variety of designs using a cosmetic ingredient, and which also enables decoration in a simplified method using a printing technique or the like. The present invention pertains to an oil-based solid cosmetic product which has a transparent oil-based base (A) and at least one decorative layer (B), and which is characterized in that: the transparent oil-based base (A) contains a thickener (a1) and a liquid oil (a2); the decorative layer (B) contains a powder component (b1); and the powder component (b1) contains at least one type of powder that has a higher refractive index than that of the liquid oil (a2).

8 Claims, 2 Drawing Sheets

OIL-BASED COSMETIC PRODUCT HAVING DECORATIVE LAYER

CROSS-REFERENCE TO RELATED APPLICATIONS

This application is the U.S. National Stage of PCT/JP2019/051206, filed Dec. 26, 2019, which claims priority to JP 2018-244017, filed Dec. 27, 2018.

TECHNICAL FIELD

The present invention relates to a decorated oil-based cosmetic product. More specifically, the present invention relates to a transparent oil-based cosmetic product having a decorative layer formed to be visible from the outside of a transparent oil-based base constituting the cosmetic product, and having excellent aesthetics.

BACKGROUND ART

Various proposals have been made to decorate the surface of solid powder cosmetic products such as foundation to make their appearance beautiful. For example, Patent Document 1 discloses a decorating powder composition for drawing characters, patterns, or the like on the surface of a cosmetic product using a printing technique, wherein a powder surface-treated with a silane compound or a silazane compound can delicately and clearly print patterns and characters exhibiting gloss.

Meanwhile, improvements on the usability such as good spreadability and suppression of stickiness while maintaining their transparency are being actively made on transparent oil-based cosmetic products. For example, in Patent Document 2, problems of usability such as poor spreadability upon application and reduced transparency over time are solved by combining 12-hydroxystearic acid with a dextrin fatty acid ester. However, attempts to decorate transparent cosmetic products are limited, and while Patent Document 2 describes a transparent lipstick and the like in which pigments are dispersed throughout the transparent cosmetic product, they are not decorated in a substantial way.

As an example of decoration of transparent cosmetic products, Patent Document 3 discloses a multicolored cosmetic product that forms a gradation pattern when viewed from outside of a transparent container by forming, in the transparent container, a transparent cosmetic layer having a bowl-shaped recess on the upper surface, on top of which cosmetic products colored in different colors are laminated. Patent Document 4 discloses a stick-shaped oil-based solid cosmetic product provided with a transparent outer layer part around a colored inner layer part. More recently, transparent lipsticks in which flower replicas and gold powder are incorporated are also commercially available (trade name: Kailijumei Tint Flower Lip).

However, with the above prior art, only one design can be used for decoration. In particular, the above commercial product incorporates a decoration made of a replica manufactured with components other than cosmetic ingredients, and therefore takes time and effort to manufacture.

CITATION LIST

Patent Document

Patent Document 1: WO2017/073263
Patent Document 2: Japanese Patent No. 3657148
Patent Document 3: Japanese Patent No. 4926515
Patent Document 4: Japanese Patent Laid-Open No. 2017-95452

SUMMARY OF INVENTION

Technical Problem

Accordingly, the object of the present invention is to provide a novel transparent oil-based cosmetic product which, when decorating the transparent oil-based cosmetic product, can be decorated with a variety of designs using cosmetic ingredients, and can be easily decorated using a printing technique or the like.

Solution to Problem

The present inventors have solved the above problems by incorporating a powder having a refractive index higher than that of a liquid oil contained in an oil-based cosmetic product in the powder component used for decorating the transparent oil-based cosmetic product, and have found that a cosmetic product having excellent aesthetics can be obtained, in which a decorative layer of a wide variety of designs can be easily formed and is clearly visible from the outside of the cosmetic product, thereby completing the present invention.

That is, the present invention provides:
an oil-based solid cosmetic product comprising a transparent oil-based base
(A) and at least one decorative layer (B),
wherein the transparent oil-based base (A) contains a thickener (a1) and a liquid oil (a2);
the decorative layer (B) contains a powder component (b1), and
the powder component (b1) contains at least one powder having a refractive index higher than that of the liquid oil (a2).

Advantageous Effects of Invention

In the oil-based solid cosmetic product according to the present invention (hereinafter, also simply referred to as "oil-based cosmetic product"), the refractive index of the powder contained in the decorative layer is set higher than the refractive index of the liquid oil of the transparent oil-based base, which allows the decorative layer to be clearly visible when viewed from the outside of the cosmetic product, and to have excellent aesthetics. Moreover, both the transparent oil-based base and the decorative layer can be composed of only cosmetic ingredients, and the whole cosmetic product including the decorative layer can be used as it is. Furthermore, the oil-based cosmetic product of the present invention can be easily produced using an existing device or the like.

BRIEF DESCRIPTION OF DRAWINGS

FIG. 1 (B) is a cross-sectional view taken along line X-X' of the top view.

DESCRIPTION OF EMBODIMENTS

Hereinafter, the oil-based cosmetic product of the present invention will be described in detail.

Figure 1:
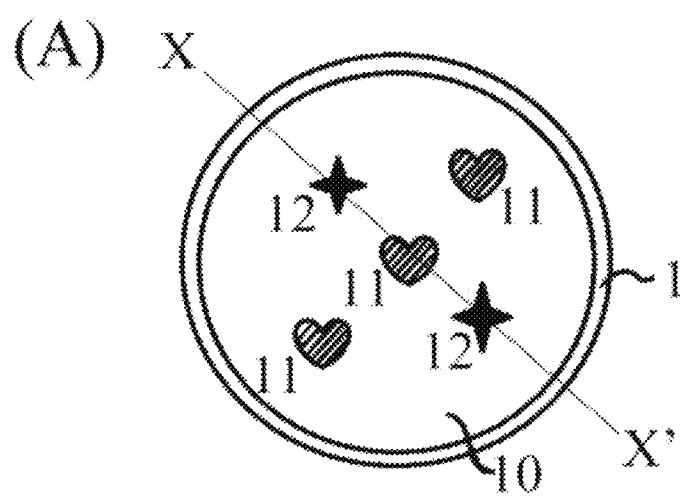
FIG. 1 (A) is a top view of an example of the oil-based cosmetic product of the present invention.
Figure 1:
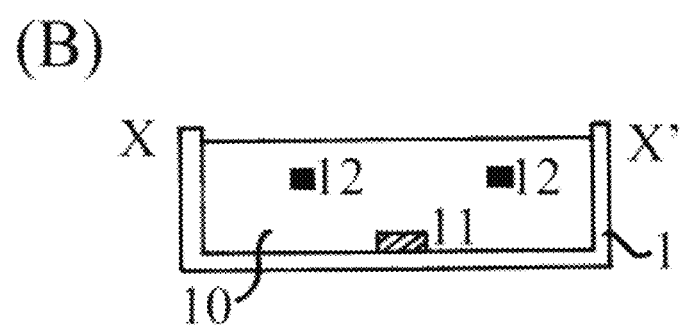

FIG. 1 is a schematic diagram showing an example of the oil-based cosmetic product of the present invention. FIG. 1(A) is a top view and FIG. 1(B) is a cross-sectional view.

The cosmetic product shown in FIG. 1 is filled into a flat plate container 1 and has a transparent oil-based base 10, a first decorative layer 11, and a second decorative layer 12.

When viewed from the upper surface, the first decorative layer 11 consists of a plurality of (three in FIG. 1) heart-shaped layers arranged apart from each other on a straight line, and the plurality of layers are provided on the same plane (the bottom of the container).

When viewed from the upper surface, the second decorative layer 12 consists of a plurality of (two in FIG. 1) star-shaped layers arranged apart from each other on a straight line, and the plurality of layers are provided on the same plane (the bottom of the container and the plane that is not in contact with the surface of the cosmetic product).

In the oil-based cosmetic product of the example shown in FIG. 1, the first decorative layer and the second decorative layer are formed in different colors.

The part other than the first and second decorative layers in the oil-based cosmetic product of FIG. 1 is composed of the transparent oil-based base 10.

The cosmetic product shown in FIG. 1 is an example of the oil-based cosmetic product of the present invention, and does not limit the scope of the present invention in any way. A wide variety of changes are possible in the present invention.

For example, one or more decorative layers may be provided on the same plane or on a plurality of different planes, and the shape, color, size and thickness may be the same or different. Moreover, the decorative layer may be provided on the bottom of the container in the same way as the first decorative layer of FIG. 1, on the surface of the transparent base, or inside the transparent oil-based base in the same way as the second decorative layer in FIG. 1.

In the oil-based cosmetic product, the refractive index of the powder contained in the decorative layer is set higher than the refractive index of the liquid oil of the transparent oil-based base, which allows the outer edge of the decorative layer to be clearly visible from the outside of the cosmetic product and to have excellent aesthetics. Furthermore, when the decorative layer is provided inside the transparent oil-based base as in the example shown in FIG. 1, or when it is provided on the surface of the transparent oil-based base, part of the light irradiated from above the cosmetic product is absorbed by the decorative layer, which projects the decorative layer onto the bottom of the container and the like, and makes its shadow visible from the outside of the cosmetic product. As a result, a cosmetic which shows the beauty created not only by the shape and color of the decorative layer itself, but also by the light and shadow, is obtained.

Transparent Oil-Based Base (A)

The transparent oil-based base constituting the oil-based cosmetic product of the present invention contains a thickener (a1) and a liquid oil (a2).

The thickener (or gelling component) (a1) is not particularly limited as long as it is a cosmetic ingredient having the effect of thickening the liquid oil by being dissolved in the liquid oil or swollen with the liquid oil. Examples thereof include a dextrin fatty acid ester, a sucrose fatty acid ester, a glyceryl fatty acid ester, an amino acid-based gelling agent, a fatty acid such as 12-hydroxystearic acid or a salt thereof, and an organically modified clay mineral. In the present invention, a dextrin fatty acid ester, especially dextrin palmitate, is preferably used.

The dextrin fatty acid ester is preferably represented by the following formula (1):

[Formula 1]

$$A\text{-}(\text{—O—CO—R})_n \quad (1)$$

wherein A is a residue obtained by removing n hydroxyl groups from dextrin, R is a linear or branched alkyl group having 3 to 30 carbon atoms, and n is an integer of 1 or more.

Specific examples of R in the above formula (1) include a linear alkyl group such as a propyl group, a butyl group, a pentyl group, a hexyl group, a heptyl group, an octyl group, a nonyl group, a decyl group, an undecyl group, a dodecyl group, a tridecyl group, a myristyl group, a pentadecyl group, a hexadecyl group and an octadecyl group, and a branched alkyl group such as a 2-ethylhexyl group, a 2-hexyldecyl group, a 2-decylmyristyl group, an isostearyl group and a 2,7-dimethylhexadecyl group.

The molecular weight of the dextrin fatty acid ester used in the present invention is not particularly limited, but is preferably 1,000 to 300,000, and more preferably 1,000 to 100,000.

Specific compound names included in the dextrin fatty acid ester represented by the general formula (1) include dextrin octanoate, dextrin decanoate, dextrin laurate, dextrin myristate, dextrin stearate, dextrin behenate, dextrin cocoate, dextrin palmitate, dextrin 2-ethylhexanoate, and dextrin myristate/palmitate.

A sucrose fatty acid ester in which the fatty acid is linear or branched, saturated or unsaturated and has 12 to 22 carbon atoms can be preferably used. Specific examples thereof include sucrose caprylate ester, sucrose caprate ester, sucrose laurate ester, sucrose myristate ester, sucrose palmitate ester, sucrose stearate ester, sucrose oleate ester, and sucrose erucate ester.

The glyceryl fatty acid ester is an esterification product obtained by reacting glycerol, a dibasic acid having 18 to 28 carbon atoms and a fatty acid having 8 to 28 carbon atoms (excluding a dibasic acid), and can be used without any particular limitation as long as it is commonly used in cosmetic products. Specific examples thereof include glyceryl behenate/isostearate/eicosandioate, glyceryl behenate/eicosandioate, and polyglyceryl-10 behenate/eicosandioate.

Examples of the amino acid-based gelling agent include dibutyl lauroyl glutamide, dibutyl ethylhexanoyl glutamide, polyamide-8, and polyamide-3.

Examples of the fatty acid (solid at normal temperature) include myristic acid, palmitic acid, stearic acid, behenic acid, and 12-hydroxystearic acid. Examples of the salt of the fatty acid include a calcium salt, a magnesium salt, and an aluminum salt of these fatty acids.

Representative examples of the organically modified clay mineral include dimethyl distearyl ammonium hectorite, dimethyl alkyl ammonium hectorite, benzyl dimethyl stearyl ammonium hectorite, and distearyl dimethyl ammonium chloride-treated aluminum magnesium silicate. Examples of commercial products include BENTONE 27 (benzyldimethylstearylammonium chloride-treated hectorite: manufactured by Elementis Japan) and BENTONE 38 (distearyldimethylammonium chloride-treated hectorite: manufactured by Elementis Japan).

The content of the thickener (a1) in the cosmetic product of the present invention is usually 0.1 to 30 mass %, preferably 1 to 25 mass %, and more preferably 5 to 20 mass % based on the total amount of the transparent oil-based base. If the content is less than 0.1 mass %, the hardness of the transparent oil-based base becomes extremely low, which makes it difficult to support the decorative layer, and if the content exceeds 30 mass %, uniform filling into the container becomes difficult.

Liquid Oil (a2)

The liquid oil used in the present invention is not particularly limited as long as it can be thickened (gelled) by the thickener to form a transparent oil-based base, and can be selected from oil components which are in liquid form at normal temperature (25° C.) and conventionally blended in cosmetic products. As a representative example, a liquid oil selected from hydrocarbon oils, ester oils, silicone oils, and liquid fats and oils is preferably used. Specific examples thereof are shown below, but are not limited thereto.

Examples of the hydrocarbon oil include liquid paraffin, hydrogenated polydecene, squalane, pristane, paraffin, squalene, triethylhexanoin, α-olefin oligomer, isododecane, isohexadecane, and light isoparaffin.

Examples of the ester oil include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprate, diisostearyl malate, glyceryl di-2-heptylundecanoate, trimethylolpropane tri-2-ethylhexanoate, pentaerythritol tetra-2-ethylhexanoate, glyceryl tri-2-ethylhexanoate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, isodecyl neopentanoate, 2-ethylhexyl succinate, ethyl acetate, butyl acetate, triethyl citrate, and caprylic/capric triglyceride.

Examples of the silicone oil include a linear polysiloxane such as dimethylpolysiloxane, methylphenylpolysiloxane, methyl hydrogen polysiloxane, and diphenylsiloxy phenyl trimethicone, and a cyclic polysiloxane such as decamethylcyclopentasiloxane, octamethylcyclotetrasiloxane, and hexamethylcyclotrisiloxane.

Examples of the liquid fat or oil include avocado oil, camellia japonica seed oil, turtle oil, macadamia nut oil, corn oil, mink oil, olive oil, rapeseed oil, egg yolk oil, sesame oil, apricot kernel oil, wheat germ oil, sasanqua oil, castor oil, flaxseed oil, safflower oil, cotton seed oil, perilla oil, soybean oil, peanut oil, Camellia sinensis seed oil, torreya nucifera seed oil, rice bran oil, tung oil, Japanese tung oil, jojoba oil, germ oil, triglycerol, glyceryl trioctanoate, and glyceryl triisopalmitate.

The liquid oils (a2) may be used alone or in combination of two or more, but are preferably blended so that the weighted average value of the refractive index of each liquid oil to be blended (this value is defined as the "refractive index of the liquid oil" in the present invention) be in the range of 1.4 to 1.6, and more preferably so that the refractive index of the liquid oil be 1.42 to 1.52.

As the refractive index of the oil in the present invention, for example, the value obtained by measuring 2 g of oil placed on a glass plate and kneaded with a metal spatula until it becomes a homogeneous slurry with a high-precision Abbe refractometer (manufactured by ATAGO, type: 3T) can be used.

The content of the liquid oil (a2) is not particularly limited, but is usually in the range of 20 to 99.5 mass %, preferably 50 to 90 mass % based on the total amount of the transparent oil-based base, and is appropriately determined according to the form, hardness, or the like of the target cosmetic product.

In addition to the above thickener (a1) and liquid oil (a2), the transparent oil-based base of the present invention can be blended with other optional components as long as it does not impair the effects of the present invention. Examples of the other optional components include, but are not limited to, a solid or semi-solid oil component, a moisturizing agent, an aqueous component, a preservative, an antioxidant, an ultraviolet absorber, a polymer, a surfactant, a colorant, a dye, a pigment, an antifoamer (simethicone, etc.), various agents (tocopherol, etc.), a lower alcohol (less than 6 carbon atoms), a solvent, and a fragrance.

The solid or semi-solid oil component is not particularly limited as long as it can be blended in a cosmetic product. Examples thereof include a solid fat or oil, a wax, a hydrocarbon oil, and a higher alcohol.

Examples of the solid fat or oil include cacao butter, coconut oil, horse oil, hydrogenated coconut oil, palm oil, beef tallow, sheep tallow, hardened beef tallow, palm kernel oil, lard, beef bone fat, Japan wax kernel oil, hydrogenated oil, Neatsfoot oil, Japan wax, and hydrogenated castor oil.

Examples of the wax include beeswax, candelilla wax, cotton wax, carnauba wax, bayberry wax, insect wax, whale wax, montan wax, rice bran wax, lanolin, kapok wax, liquid lanolin, sugar cane wax, isopropyl lanolate, reduced lanolin, jojoba wax, hard lanolin, shellac wax, POE lanolin alcohol ether, POE lanolin alcohol acetate, POE cholesterol ether, polyethylene glycol lanolate, and POE hydrogenated lanolin alcohol ether.

Examples of the hydrocarbon oil (solid or semi-solid) include ozokerite, ceresin, petrolatum, and microcrystalline wax.

Examples of the higher alcohol include a linear alcohol such as lauryl alcohol, cetyl alcohol, stearyl alcohol, behenyl alcohol, myristyl alcohol, oleyl alcohol, and cetostearyl alcohol, and a branched alcohol such as monostearyl glyceryl ether (batyl alcohol), 2-decyltetradecinol, lanolin alcohol, cholesterol, phytosterol, hexyldodecanol, and octyldodecanol.

Examples of the moisturizing agent include polyhydric alcohols and sugar alcohols, and specific examples thereof include a glycol such as dipropylene glycol and 1,3-butylene glycol, glycerin, mannitol, and sorbitol.

Here, the term "transparent" in the present invention includes the range from "transparent" to "translucent" in the sense generally used in the field of cosmetic products as long as the decorative layer is visible from the outside of the cosmetic product. For example, an oil-based base which shows a light transmittance at 900 nm of at least 50% on a spectrophotometer when filled into a cell having an optical path length of 10 mm, cooled, solidified, and then left at 25° C. for 1 hour, may be defined as a "transparent oil-based base" in the present invention.

The transparent oil-based base (A) in the present invention may be in a form consisting of only oil-based components, or may be in an emulsified form such as a water-in-oil type or an oil-in-water-in-oil type containing an aqueous component, as long as the above requirement that the oil-based base should be "transparent" is satisfied. Moreover, it may be colorless or colored as long as it remains transparent. These oil-based bases can be produced using methods widely used for various forms of cosmetic products.

The transparent oil-based base (A) of the present invention is preferably solid. The term "solid" in the present invention means a composition having no fluidity at normal temperature (25° C.) under normal pressure. Moreover, a composition having a hardness of 50 to 300 measured at 25° C. with a rheometer (3 mmφ, 1.0 mm penetration, 2K range, 2 cm/min) may be defined as "solid" in the present invention. When the hardness is less than 50, the oil-based base is no longer able to support the decorative layer, and if it exceeds 300, the oil-based base no longer spreads uniformly when filled into a container, and the formation of the decorative layer on its surface becomes difficult.

Decorative Layer (B)

The decorative layer (B) in the oil-based cosmetic product of the present invention contains a powder component (b1). The powder component (b1) contains at least one powder having a refractive index higher than that of the liquid oil (a2).

The powder component (b1) is an essential component for exhibiting the decorative effect of the decorative layer, and is preferably a powder selected from inorganic pigments such as white pigments, coloring pigments, and pearly pigments, and organic powders that can be blended in cosmetic products.

Specific examples of the powder that can be blended include, but are not limited to, an inorganic powder such as talc, kaolin, mica, sericite, muscovite, biotite, phlogopite, synthetic mica, vermiculite, magnesium carbonate, calcium carbonate, aluminum silicate, barium silicate, calcium silicate, magnesium silicate, metal tungstate, magnesium, silica, zeolite, cerium oxide, zirconium oxide, tin oxide, aluminum oxide, magnesium oxide, barium sulfate, barium titanate, calcined calcium sulfate, calcined gypsum, calcium phosphate, fluorapatite, hydroxyapatite, ceramic powder, and metal soaps (zinc myristate, calcium palmitate, aluminum stearate, etc.); an organic powder such as polyamide resin powder (nylon powder, etc.), polyethylene powder, polymethyl methacrylate powder, polystyrene powder, PMMA powder, styrene-acrylic acid copolymer resin powder, benzoguanamine resin powder, polytetrafluoroethylene powder, and cellulose powder; an inorganic white pigment such as titanium oxide and zinc oxide; an inorganic red pigment such as iron oxide (red iron oxide) and iron titanate; an inorganic brown pigment such as γ-iron oxide; an inorganic yellow pigment such as yellow iron oxide and yellow ocher; an inorganic black pigment such as black iron oxide, carbon, and lower titanium oxide; an inorganic purple pigment such as mango violet and cobalt violet; an inorganic green pigment such as chromium oxide, chromium hydroxide and cobalt titanate, an inorganic blue pigment such as ultramarine and iron blue; a pearl pigment such as titanium oxide-coated mica, titanium oxide-coated bismuth oxychloride, titanium oxide-coated talc, colored titanium oxide-coated mica, bismuth oxychloride, and fish scale guanine; a metal powder pigment such as aluminum powder and copper powder; an organic pigment such as Red No. 202, Red No. 205, Red No. 220, Red No. 228, Red No. 405, Orange No. 203, Orange No. 204, Yellow No. 205, Yellow No. 401, and Blue No. 404; an organic pigment such as zirconium, barium and aluminum lake such as Red No. 3, Red No. 104, Red No. 227, Red No. 401, Orange No. 205, Yellow No. 4, Yellow No. 202, Green No. 3 and Blue No. 1; and a natural colorant such as chlorophyll and β-carotene.

The powders may be used alone or in combination of two or more. However, the powder component (b1) contains at least one powder having a refractive index higher than that of the liquid oil (a2) contained in the transparent oil-based base (A) (hereinafter, also referred to as "high-refractive-index powder").

As a high-refractive-index powder, a powder having a refractive index higher than that of the liquid oil (a2) preferably by 0.01 or more, more preferably 0.05 or more, still more preferably 0.1 or more, and most preferably 0.5 or more is selected.

The high-refractive-index powder is not particularly limited, but is preferably selected from powders having a refractive index of 1.45 or more. Specific examples of powders having a refractive index of 1.45 or more include titanium oxide (rutile-type and anatase-type), barium titanate, cerium oxide, zirconium oxide, bismuth oxychloride, zinc oxide, tin oxide, aluminum oxide, magnesium oxide, barium sulfate, polystyrene, kaolin, mica, talc, nylon, PMMA, and silica.

The powder component (b1) should contain at least one high-refractive-index powder, but the proportion of high-refractive-index powder in the powder component (b1) is preferably 50 mass % or more, 70 mass % or more, or 80 mass % or more, and the powder component (b1) may be composed of only high-refractive-index powder.

In the present invention, it is preferable to form the decorative layer by preparing a dispersion (hereinafter, also referred to as "ink composition") obtained by dispersing the powder component (b1) in a medium (b2) in which the powder component can be dispersed, and spraying or the like the ink composition.

The dispersing medium (b2) in the ink composition is not particularly limited as long as it is a medium having a fluidity allowing the dispersion of the powder component (b1), but a medium having a low boiling point, for example, a lower alcohol having 3 or less carbon atoms such as ethanol is preferable when the drying rate at the formation of the decorative layer is considered. In addition, when the formation of the decorative layer on the surface of the transparent oil-based base (A) is considered, it is preferable to select a medium having low compatibility with the oil component blended in the transparent oil-based base (A) in order to prevent bleeding of the decorative layer (B).

In addition to the powder component (b1) and the dispersing medium (b2), the ink composition preferably contains a binder component that binds the powders to each other in the decorative layer. A moisturizing agent such as glycerin and a thickener such as dimethylacrylamide/sodium acryloyldimethyltaurate crosspolymer may also be appropriately contained.

The oil-based cosmetic product of the present invention is produced through a step of forming a decorative layer on the bottom of a container or on the surface of the transparent oil-based base filled into the container. In forming the decorative layer, it is convenient and preferable to use the ink composition and apply it by coating, spraying, printing or the like so as to obtain the intended shape/pattern.

For the formation of the decorative layer using the ink composition, for example, a method using a stencil technique which uses a paper pattern in which the intended shape or pattern has been cut out, applies the ink composition over the paper pattern, then removes the paper pattern, a method of spraying the ink composition using a similar paper pattern, a method using a screen printing technique, a method of drawing with the ink composition using an inkjet printer, and the like can be used.

When considering a case in which the ink composition is used to form the decorative layer as described above and is applied via a nozzle such as that of a spray or an inkjet printer, it is preferable to keep the viscosity of the ink composition to 10000 mPa·s or less, preferably 8000 mPa·s or less from the viewpoint of preventing nozzle clogging.

Moreover, the content of the powder component (b1) in the ink composition is not particularly limited, but is preferably 5 to 20 mass %, more preferably 7 to 15 mass % based on the total amount of the ink composition. Furthermore, from the viewpoint of preventing nozzle clogging, the average particle size of the powder contained in (b1) is preferably 200 m or less, and more preferably 100 m or less.

The present invention provides a method for producing the oil-based cosmetic product of the present invention described above. The method includes:

(1) a step of forming a decorative layer (B) by drawing with an ink composition in which the powder component (b1) is dispersed in a dispersing medium (b2); and
(2) a step of filling the transparent oil-based base (A) into a container.

Hereinafter, a method for producing the oil-based cosmetic product of the present invention by using a stencil technique for the formation of the decorative layer will be described with reference to FIG. 1.

First, the first decorative layer 11 is formed by applying a stencil paper pattern (a paper pattern in which three heart shapes have been cut out) to the bottom of the flat plate container 1, and printing the ink composition for forming the first decorative layer 11 (first ink composition). After appropriate drying, the transparent oil-based base 10 is filled up to the height of the bottom of the second decorative layer 12. Next, the second decorative layer 12 is formed by printing the ink composition for forming the second decorative layer 12 (second ink composition) by a stencil technique using a paper pattern in which two star shapes have been cut out. After appropriately drying, the transparent oil-based base 10 is filled from above until the container is full.

As described above, a transparent oil-based cosmetic product having a plurality of decorative layers can be produced. The thickness of the decorative layer is not particularly limited, but is usually 0.01 to 1 mm.

In FIG. 1, the first ink composition and the second ink composition contain powder components having different colors from each other.

Moreover, the production method using the above stencil technique can be changed to an automated production method using a screen printing device, an inkjet printing device, or the like.

Figure 2:
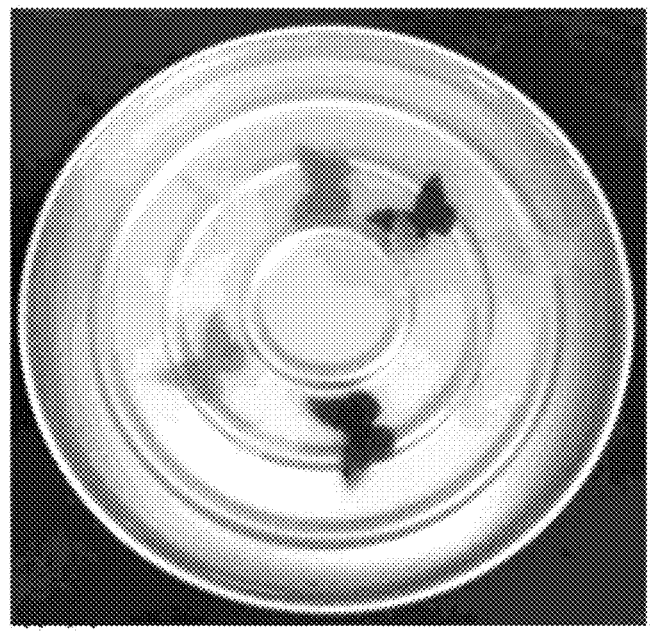
FIG. 2 is a photograph showing the appearance of another example of the oil-based cosmetic product of the present invention.

FIG. 2 is a photograph showing another example of the oil-based cosmetic product of the present invention produced according to the above method. The cosmetic product in this example has a butterfly-shaped decorative layer arranged three-dimensionally with three different colors.

Although not apparent in the photograph of FIG. 2, the whole oil-based cosmetic product is transparent and has the visual effects of having a peculiar appearance with a lamellar (membrane-like) decorative layer of a plurality of colors inside, and having a shadow formed under the decorative layer when exposed to light from the surface of the cosmetic product, which gives the appearance that the decorative layer is three-dimensionally floating.

The oil-based cosmetic product of the present invention makes use of the unique appearance (aesthetics) described above and is particularly suitable to be provided as a makeup cosmetic product. While not particularly limited, it is preferably provided as a lipstick, a base, an eye base (a base for eye shadow), or the like.

EXAMPLES

Hereinafter, the present invention will be further described with reference to Examples, but the present invention is not limited to Examples. Unless otherwise specified, the content is indicated in mass %.

Transparent oil-based cosmetic products having a decorative layer were produced using the transparent oil-based base having the composition shown in Table 1 below and the ink compositions for forming the decorative layer having the compositions described in Table 2.

TABLE 1

| Category | Blended component (Refractive Index) | Content (mass %) |
| --- | --- | --- |
| Thickener (a1) | Dextrin Palmitate | 15 |
| Oil Component (a2) | Hydrogenated Polydecene (1.46) | 30 |
| | Diphenylsiloxy Phenyl Trimethicone (1.50) | 10 |
| | Isopropyl Sebacate (1.43) | 10 |
| | Caprylic/Capric Triglyceride (1.45) | 9.41 |
| | Neopentyl Glycol Dicaprate (1.445) | 10 |
| | Isopropyl Myristate (1.435) | 10 |
| | Isodecyl Neopentanoate (1.43) | 5 |
| Others | Simeticone | 0.05 |
| | Tocopherol | 0.04 |
| | Dipropylene Glycol | 0.5 |
| | Total | 100 |
| | Refractive Index of Oil Component | 1.454 |

TABLE 2

| | Example A | Example B | Example C |
| --- | --- | --- | --- |
| Ethanol | 87.3 | 87.3 | 87.3 |
| Dimethyl Acrylamide/Sodium Acryloyldimethyl Taurate Cross Polymer | 1.2 | 1.2 | 1.2 |
| Nitroglycerin | 1 | 1 | 1 |
| Phenoxyethanol | 0.5 | 0.5 | 0.5 |
| Red Iron Oxide-Coated Mica Titanium [Refractive Index: 2.3 to 2.6] | 10 | — | — |
| Red Iron Oxide-Coated Mica Titanium [Refractive Index: 2.3 to 2.6] (Methyl Polysiloxane Surface Treated) | — | 10 | — |
| Silica [Refractive Index: 1.45] | — | — | 10 |
| Total | 100 | 100 | 100 |
| Viscosity (immediately after production) [mPa · s] | 7020 | 7180 | Not measured |
| Viscosity (after 3 days) [mPa · s] | 9820 | 7210 | Not measured |

In the transparent oil-based cosmetic products having a decorative layer formed by using the ink compositions of Examples A and B described in Table 2 (Examples 1 and 2, respectively), the decorative layer exhibiting a bright red color was clearly visible from the outside of the cosmetic product regardless of with or without hydrophobization of the surface of the blended powder components.

Figure 3:
FIG. 3 is a photograph showing the appearance of Comparative Example 1.

However, when the ink composition having the composition described in Example C of Table 2 was used to draw on the bottom of the container to form the decorative layer, over which the transparent oil-based base of Table 1 was filled (Comparative Example 1), the decorative layer contained only powder (silica) having a refractive index lower than that of the liquid oil, and therefore the outline of the decorative layer was blurred and not clearly visible, resulting in poor aesthetics (See FIG. 3).

The invention claimed is:

1. An oil-based solid cosmetic product filled in a container and comprising:
   (A) a transparent oil-based base; and
   (B) at least one decorative layer;
   wherein the (B) decorative layer is formed as a membrane provided under and/or in the (A) transparent oil-based base,
   wherein the transparent oil-based base (A) comprises (a1) a thickener and (a2) a liquid oil;
   wherein the decorative layer (B) comprises (b1) a powder component; and
   wherein the powder component (b1) comprises a powder having a refractive index higher than that of the liquid oil (a2).

2. The oil-based solid cosmetic product according to claim 1, wherein the powder having a refractive index higher than that of the liquid oil (a2) has a refractive index higher at least 0.01 than that of the liquid oil (a2).

3. The oil-based solid cosmetic product according to claim 1, wherein the liquid oil (a2) consists of an oil having a refractive index of 1.42 to 1.52.

4. The oil-based solid cosmetic product according to claim 1, wherein the powder component (b1) comprises a powder having a refractive index higher than 1.45.

5. The oil-based solid cosmetic product according to claim 1, wherein the (a1) thickener is dextrin palmitate.

6. The oil-based solid cosmetic product according to claim 1, wherein the (a2) liquid oil is at least one selected from hydrocarbon oils, ester oils, silicone oils, and liquid fats.

7. A method for producing the oil-based solid cosmetic product according to claim 1, comprising:
   (1) a step of preparing (A) a transparent oil-based base by mixing components comprising (a1) a thickener and (a2) a liquid oil;
   (2) a step of preparing an ink composition by dispersing the powder component (b1) in a dispersing medium;
   (3) a step of filling a part of the (A) transparent oil-based base into a container;
   (4) a step of forming a decorative layer (B) by drawing with the ink composition on the (A) transparent oil-based base; and
   (5) a step of filling another part of the (A) transparent oil-based base into the container.

8. The method for producing the oil-based solid cosmetic according to claim 7, further comprising:
   a step of forming a decorative layer (B) by drawing with the ink composition on the bottom of the container before the step (3).

* * * * *